United States Patent [19]
Rinker et al.

[11] Patent Number: 6,002,040
[45] Date of Patent: Dec. 14, 1999

[54] REDUCED PRESSURE DROP IN ACRYLONITRILE ABSORBER VIA DIRECT CONTACT SPRAY HEAT EXCHANGE

[75] Inventors: Jeffrey Earle Rinker, Hudson; Paul Trigg Wachtendorf, Wapakoneta, both of Ohio; Vincent Astor Little, III, Houston, Tex.; Sanjay Purushottam Godbole, Solon, Ohio

[73] Assignee: The Standard Oil Company, Chicago, Ill.

[21] Appl. No.: 09/078,789

[22] Filed: May 14, 1998

[51] Int. Cl.$^6$ .................................................. C07C 255/00
[52] U.S. Cl. ........................... 558/320; 558/435; 558/462
[58] Field of Search .................................... 558/320, 435, 558/462

[56] References Cited

FOREIGN PATENT DOCUMENTS

3236304 A1   4/1984   Germany .

*Primary Examiner*—Johann Richter
*Assistant Examiner*—Joseph Murray
*Attorney, Agent, or Firm*—Thomas E. Nemo; Stephan L. Hensley

[57] ABSTRACT

A process for manufacturing acrylonitrile comprising reacting propylene, ammonia and oxygen in a reactor zone in the presence of a catalyst to produce a reactor effluent containing crude acrylonitrile, transferring the reactor effluent containing crude acrylonitrile to a quench column wherein the reactor effluent containing crude acrylonitrile is contacted with an aqueous stream to cool the reactor effluent, transferring the cooled reactor effluent containing the crude acrylonitrile to an absorption column wherein the reactor effluent containing crude acrylonitrile is contacted with a second aqueous stream to separate and remove the crude acrylonitrile as a bottom stream from the absorption column, transferring the bottom stream containing the crude acrylonitrile to a recovery and purification section where the acrylonitrile is recovered and purified, wherein the improvement comprises supplying the second aqueous stream to the absorption column by means of liquid spray nozzles.

5 Claims, 1 Drawing Sheet

REDUCED PRESSURE DROP IN ACRYLONITRILE ABSORBER VIA DIRECT CONTACT SPRAY HEAT EXCHANGE

BACKGROUND OF THE INVENTION

Field of the Invention

The present invention is directed to the manufacture of acrylonitrile. In particular, the present invention is directed to an improved process for the manufacture of acrylonitrile utilizing a fluid bed reactor.

The process for manufacturing acrylonitrile in a fluid bed reactor has been practiced commercially since the early 1960's. Typically, the reactor effluent from the propylene ammoxidation reaction in a fluid bed reactor is passed through a quench column, absorption column and recovery stripper columns to purify and recover the acrylonitrile product. Generally, a water stream is used to absorb the product organics (acrylonitrile, acetonitrile and HCN) from the vapor stream in the absorption column. The product organics removed in the absorption column are then stripped from the water stream in the recovery stripper columns. Typically, the absorption column contains three sections: (1) a lower heat transfer zone where hot gases from the quench are cooled by direct heat exchange with cold water; (2) an absorption zone where organics in the reaction gases are absorbed into a chilled water (the resultant water, rich with organic product is called a "rich water"); and (3) an upper heat transfer zone where incoming water is cooled by direct exchange with the cold strip gas. In prior art procedures, the internals for these three sections of the absorption column typically comprise refractionation trays or structured packing or random packing. The present invention is directed to an improved process for the manufacture and recovery of acrylonitrile which results in improved run time due to elimination of polymer fouling problems in the absorption column.

SUMMARY OF THE INVENTION

It is the primary object of the present invention to provide an improved process for the manufacture of acrylonitrile.

It is another object of the present invention to provide an improved process for the manufacture of acrylonitrile utilizing a fluid bed reactor.

It is still another object of the present invention to provide an improved recovery and purification procedure for acrylonitrile produced from a fluid bed reactor.

Additional objects and advantages of the invention will be set forth in part in the description which follows, and, in part, will be obvious from the description or may be learned by the practice of the invention. The objects and advantages of the invention may be realized and attained by means of the instrumentalities and combinations particularly pointed out in the appended claims.

To achieve the foregoing objects and in accordance with the purpose of the present invention as embodied and broadly described herein, the process of the present invention comprises reacting propylene, ammonia and oxygen in a reaction zone in the presence of a catalyst to produce a reactor effluent containing crude acrylonitrile, transferring the reactor effluent containing crude acrylonitrile to a quench column wherein the reactor effluent containing crude acrylonitrile is contacted with an aqueous stream to cool the reactor effluent, transferring the cooled reactor effluent containing the crude acrylonitrile to an absorption column wherein the reactor effluent containing the crude acrylonitrile is contacted with a second aqueous stream to separate and remove crude acrylonitrile as a bottom stream, transferring the bottom stream containing the crude acrylonitrile to a recovery column where the acrylonitrile is recovered, wherein the improvement comprises supplying the second aqueous stream to the absorption column by means of liquid spray nozzles.

In a preferred embodiment of the present invention, the process for the manufacture of acrylonitrile comprises contacting the ammonia, oxygen-containing gas and propylene in the presence of a fluid bed catalyst in a fluid bed reactor.

In a further preferred embodiment of the present invention, the spray nozzles are positioned in the bottom portion of the absorption column.

In a still further preferred embodiment of the present invention, the spray nozzles are positioned in the top heat transfer position of the absorption column.

In still another preferred embodiment of the present invention, the spray nozzles are positioned throughout the absorption column.

DETAILED DESCRIPTION OF THE INVENTION

The process of the present invention will now be described in detail with reference to the appended drawings.

The invention can be applied to any recovery and purification for acrylonitrile and methacrylonitrile that has an absorption column wherein the product is transferred from the quench column to the absorption column prior to recovery and purification of the product acrylonitrile. The specific intermediate steps associated with the recovery and purification are not critical to the present invention and within the purview of anyone having ordinary skill in the art. For example, distillation towers may be utilized in the purification of the crude acrylonitrile to produce acrylonitrile.

Figure 1:
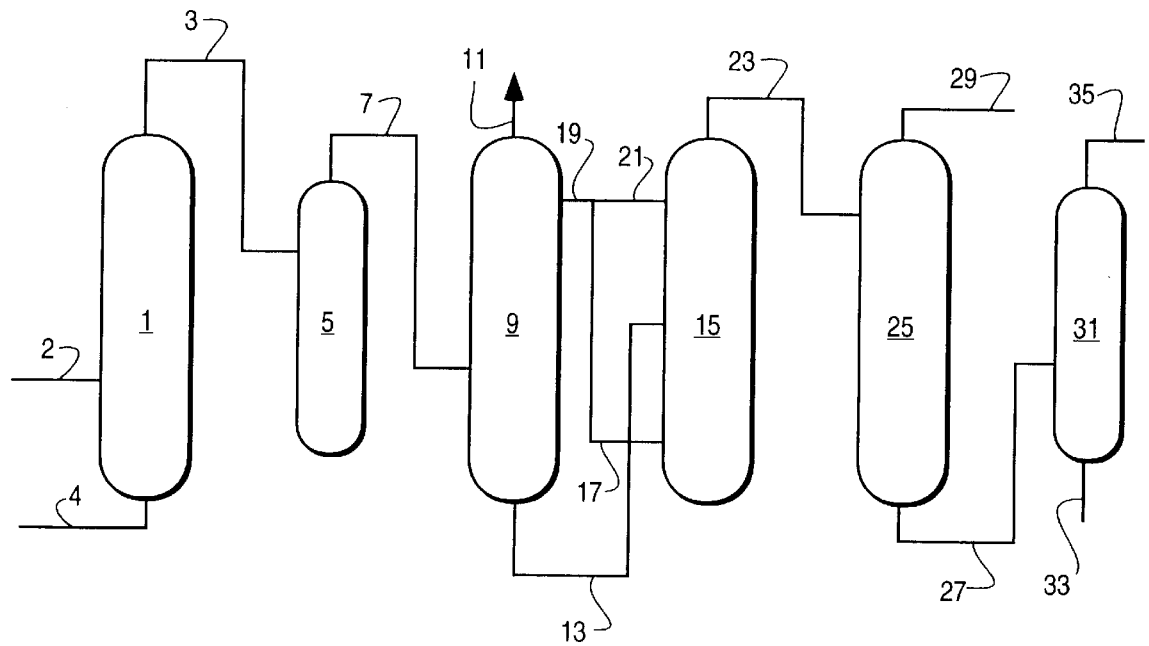
FIG. 1 is a schematic drawing of the process of the present invention.

With reference to FIG. 1, propylene and ammonia are transferred to reactor 1 via line 2 and an oxygen-containing gas (typically, air) is supplied to the reactor via line 4. The propylene, ammonia and oxygen react in the reactor (preferably, a fluid bed reactor) in the presence of a fluid bed catalyst to produce acrylonitrile. The reactor effluent containing acrylonitrile is transferred from reactor 1 via line 3 to quench 5 wherein the reactor effluents are cooled by direct contact with an aqueous stream. The cooled reactor effluent is removed from quench 5 and enters absorption column 9 via line 7 wherein an aqueous stream contacts the cooled reactor effluent to remove the crude acrylonitrile (a crude acrylonitrile is intended to refer to acrylonitrile which is containing various impurities including co-products HCN and acetonitrile) present in the reactor effluent. The crude acrylonitrile is then transferred from the absorption column 9 via line 13 to recovery column 15 wherein the crude acrylonitrile is subjected to distillation to remove certain impurities and the crude acrylonitrile is transferred via line 23 to head column 25 where further distillation takes place to separate the acrylonitrile from the co-products (i.e. HCN and acetonitrile). The recovered acrylonitrile is then removed from heads column 25 via line 27 and is further purified in product column 31. Purified acrylonitrile is removed from product column 31 via line 35 and waste is recovered for recycle via line 33. Co-product HCN is usually recovered from line 29 of heads column 25. Co-product acetonitrile is usually recovered as a side stream (not shown) from recovery column 15.

In the practice of the present invention, absorption column 9 is specifically adapted to provide a novel procedure for contacting the cooled reactor effluent gas containing acrylonitrile to remove the acrylonitrile from the reactor effluent.

Figure 2:
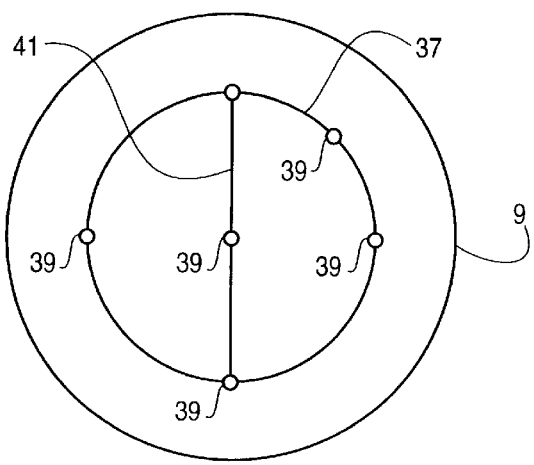
FIG. 2 is a cross sectional view of the absorption column adapted with liquid spray nozzles.

With specific reference to FIG. 2, the novel configuration for the internals of absorption column 9 are shown.

FIG. 2 is a cross sectional view of absorption column 9 and shows a preferred embodiment of the present invention. The internal section of absorption column 9 contains a circular shaped grid having a cross bar 41. Grid 37 and cross bar 41 are adapted to have liquid spray nozzles 39 positioned about the circular grid 37 and cross bar 41 in such a manner that the aqueous spray coming from nozzles 39 encompasses the entire circumference of absorption column 39 allowing for complete contact of the aqueous spray with the cooled reactor effluent gas to remove the acrylonitrile as a bottom stream via line 13 (FIG. 1). Typically, the spacing between the liquid spray nozzles is from 36 inches to 144 inches, preferably 48 inches to 90 inches. Obviously, the number of spray nozzles utilized in a column will depend on the size of the column with the objective being to ensure that the entire circumference of the column is covered. Typically, in a column having a 16 foot diameter, the number of nozzles utilized ranges from 7 to 10 depending on the size of the nozzle used. In addition, the actual configuration of the nozzles is not critical provided that substantially all of the circumference of the column is encompassed by the spray pattern emanating from the spray nozzles.

Hollow cone or full cone liquid spray nozzles may be installed in the upper and/or lower heat transfer sections of the absorption column. It is a preferred embodiment of the present invention that multiple levels of hollow cone nozzles are installed with adequate spacing between the nozzles and levels to insure total coverage of the liquid spray over the full open area of the absorption column shell.

Adequate pumped liquid circulation is introduced through the spray nozzles to accomplish the desired heat transfer in the upper and/or lower heat transfer section via direct contacting of the gas phase containing product acrylonitrile with the sprayed liquid. The pumped liquid may preferably be a slip stream of the absorption tower bottoms or a slip stream of the absorption tower side drawer and/or the absorption tower lean water and/or fresh make-up water to the absorption tower and/or process condensed from the quench.

In a further preferred embodiment of the present invention, manual or automatic control valves are installed on the supply piping to each level of spray nozzles to allow adjustment of the flow rate to each level and optimization of heat transfer.

The adaptation of the liquid spray nozzles into the internals of the absorption column in place of trays or structured or random packing has been observed to produce the following improved benefits. The use of spray nozzles leads to a lower inherent pressure drop of the spray system in the inherent lower fouling tendency of the spray system. It has been observed that absorption column packings, whether random or structured, tend to foul with polymers during operation of a recovery and purification system for acrylonitrile. The accumulated polymer deposits result in an increased column pressure drop until the column must be shut down for expensive, time-consuming cleaning. In the process of the present invention the spray system removes potential surfaces for polymer formation, thereby eliminating or substantially eliminating the polymer fouling problem. With removal or substantial elimination of the polymer fouling problem is an attendant ability to operate the system at a lower pressure. Of course, operation at a lower pressure leads to an improvement in the recovery and purification system leading to increase in yields of product acrylonitrile.

It is apparent that there has been provided in accordance with the invention a process that fully satisfies the objects and aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

What we claim as our invention is:

1. A process for manufacturing acrylonitrile comprising reacting propylene, ammonia and oxygen in a reactor zone in the presence of a catalyst to produce a reactor effluent containing crude acrylonitrile, transferring the reactor effluent containing crude acrylonitrile to a quench column wherein the reactor effluent containing crude acrylonitrile is contacted with a first aqueous stream to cool the reactor effluent, transferring the cooled reactor effluent containing the crude acrylonitrile to an absorption column wherein the reactor effluent containing crude acrylonitrile is contacted with a second aqueous stream to separate and remove the crude acrylonitrile as a bottom stream from the absorption column, transferring the bottom stream containing the crude acrylonitrile to a recovery and purification section where the acrylonitrile is recovered and purified, wherein the improvement comprises supplying the second aqueous stream to the absorption column by means of liquid spray nozzles.

2. The process of claim 1 wherein the reactor zone comprises a fluid bed reactor.

3. The process of claim 1 wherein the spray nozzles are positioned in the bottom portion of the absorption column.

4. The process of claim 1 wherein the spray nozzles are positioned in the upper portion of the absorption column.

5. The process of claim 1 wherein the spray nozzles are positioned throughout the absorption column.

* * * * *